(12) United States Patent
Moscoso et al.

(10) Patent No.: US 8,053,617 B2
(45) Date of Patent: *Nov. 8, 2011

(54) PROCESSES USING UZM-37 ALUMINOSILICATE ZEOLITE

(75) Inventors: Jaime G. Moscoso, Mount Prospect, IL (US); Deng-Yang Jan, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/157,046

(22) Filed: Jun. 9, 2011

(65) Prior Publication Data

US 2011/0245564 A1    Oct. 6, 2011

Related U.S. Application Data

(63) Continuation of application No. 12/750,939, filed on Mar. 31, 2010, now Pat. No. 7,982,084.

(51) Int. Cl.
| | |
|---|---|
| *C07C 2/66* | (2006.01) |
| *C07C 6/12* | (2006.01) |
| *C07C 4/06* | (2006.01) |
| *C07C 5/27* | (2006.01) |
| *C07C 2/58* | (2006.01) |
| *C07C 2/12* | (2006.01) |
| *C10G 47/00* | (2006.01) |
| *C10G 11/00* | (2006.01) |
| *C10G 25/00* | (2006.01) |

(52) U.S. Cl. ........ 585/467; 585/486; 585/475; 585/481; 585/722; 585/533; 208/111.01; 208/120.01; 208/27

(58) Field of Classification Search ............... 585/486, 585/475, 481, 722, 533; 208/111.01, 120.01, 208/27

See application file for complete search history.

(56) References Cited

U.S. PATENT DOCUMENTS 4,440,871 A * 4/1984 Lok et al. .................. 502/214

* cited by examiner

*Primary Examiner* — Thuan Dinh Dang
(74) *Attorney, Agent, or Firm* — Maryann Maas

(57) ABSTRACT

A new family of crystalline aluminosilicate zeolites has been synthesized. These zeolites are represented by the empirical formula.

$$M_m^{n+}R_r^+Al_{(1-x)}E_xSi_yO_z$$

where M represents a combination of potassium and sodium exchangeable cations, R is a singly charged organoammonium cation such as the propyltrimethylammonium cation and E is a framework element such as gallium. These zeolites are similar to MWW but are characterized by unique x-ray diffraction patterns and compositions and have catalytic properties for carrying out various hydrocarbon conversion processes.

1 Claim, No Drawings

PROCESSES USING UZM-37 ALUMINOSILICATE ZEOLITE

CROSS-REFERENCE TO RELATED APPLICATION

This application is a Continuation of copending application Ser. No. 12/750,939 filed Mar. 31, 2010, the contents of which are hereby incorporated by reference in its entirety.

FIELD OF THE INVENTION

This invention relates to a new family of aluminosilicate zeolites designated UZM-37. They are represented by the empirical formula of:

$$M_m^{n+}R^+_rAl_{1-x}E_xSi_yO_z$$

where M represents sodium or a combination of sodium/potassium or lithium/strontium exchangeable cations, R is a singly charged organoammonium cation such as propyltrimethylammonium hydroxide and E is a framework element such as gallium.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Topological zeolites can be used as catalysts for hydrocarbon conversion reactions, which can take place on outside surfaces as well as on internal surfaces within the pore.

In U.S. Pat. No. 4,528,171 an EU-4 zeolite is described. The template propyltrimethylammonium hydroxide is used in the synthesis of EU-4. However, the silica to alumina ratio of the product EU-4 is higher than 49.1.

In U.S. Pat. No. 6,892,511 another zeolite, UZM-15, is described. The template propyltrimethylammonium hydroxide is used in the synthesis of UZM-15, but only as an additive to another template; and not as the sole template.

In U.S. Pat. No. 7,575,737 another zeolite, UZM-27 is synthesized with a propyltrimethylammonium hydroxide template in conjunction with calcium.

Applicants have successfully prepared a new family of materials designated UZM-37. The topology of the materials is similar to that observed for MWW. The materials are prepared via the use of a simple commercially available structure directing agent, such as propyltrimethylammonium hydroxide, using the Charge Density Mismatch Approach to zeolite synthesis (U.S. Pat. No. 7,578,993). The organoammonium compounds used to make UZM-37 zeolite are non-cyclic or contain cyclic substituents and are generally quite simple. Examples of organoammonium compounds used to make UZM-37 include propyltrimethylammonium (PTMA) and isopropyltrimethylammonium (1-PTMA) cations.

SUMMARY OF THE INVENTION

As stated, the present invention relates to a new aluminosilicate zeolite designated UZM-37. Accordingly, one embodiment of the invention is a microporous crystalline zeolite having a three-dimensional framework of at least $AlO_2$ and $SiO_2$ tetrahedral units and an empirical composition in the as synthesized and anhydrous basis expressed by an empirical formula of:

$$M_m^+R^+_rAl_{1-x}E_xSi_yO_z$$

where M represents sodium or a combination of sodium/potassium or lithium/strontium exchangeable cations, "m" is the mole ratio of M to (Al+E) and varies from about 0.05 to about 2, R is a singly charged organoammonium cation propyltrimethylammonium hydroxide, "r" is the mole ratio of R to (Al+E) and has a value of about 0.25 to about 5.0, E is an element selected from the group consisting of gallium, iron, boron and mixtures thereof, "x" is the mole fraction of E and has a value from 0 to about 1.0, "y" is the mole ratio of Si to (Al+E) and varies from greater than 7 to about 20 and "z" is the mole ratio of O to (Al+E) and has a value determined by the equation:

$$z=(m+r+3+4\cdot y)/2$$

and is characterized in that it has the x-ray diffraction pattern having at least the d-spacings and intensities set forth in Table A

TABLE A

| 2θ | d (Å) | I/Io % |
|---|---|---|
| 3.22-3.48 | 25.35-27.44 | m |
| 6.62-6.92 | 12.76-13.34 | m |
| 7.12-7.39 | 11.93-12.4 | s-vs |
| 7.92-8.32 | 10.61-11.15 | m |
| 8.64-8.81 | 10.01-10.22 | m |
| 9.71-9.85 | 8.97-9.09 | m |
| 12.75-12.78 | 6.92-6.93 | w |
| 13.39-13.72 | 6.44-6.6 | w |
| 14.34-14.5 | 6.1-6.17 | w |
| 20.13-20.2 | 4.39-4.4 | m |
| 21.56-21.64 | 4.1-4.11 | m |
| 22.14-22.28 | 3.98-4.01 | m |
| 23.09-23.35 | 3.8-3.84 | m |
| 23.95-23.97 | 3.7-3.71 | w-m |
| 24.92-25.19 | 3.53-3.57 | m |
| 25.92-26.21 | 3.39-3.43 | vs |
| 26.7-26.77 | 3.32-26.7 | m |
| 28.99-29.32 | 3.04-3.07 | w-m |
| 31.51-31.64 | 2.82-2.83 | w |
| 33.3-33.69 | 2.65-2.68 | w |
| 37.68-37.94 | 2.36-2.38 | w |
| 46.05-46.29 | 1.95-1.96 | w |
| 48.78-48.94 | 1.85-1.86 | w | and is thermally stable up to a temperature of greater than 600° C. in one embodiment and 700° C. in another embodiment.

Another embodiment of the invention is a process for preparing the crystalline microporous zeolite described above. The process comprises forming a reaction mixture containing reactive sources of M, R, Al, Si and optionally E and heating the reaction mixture at a temperature of about 150° C. to about 200° C., or about 165° C. to about 185° C., for a time sufficient to form the zeolite, the reaction mixture having a composition expressed in terms of mole ratios of the oxides of:

$$aM_2O:bR_{2/p}O:1\text{-}cAl_2O_3:cE_2O_3:dSiO_2:eH_2O$$

where "a" has a value of about 0.05 to about 25, "b" has a value of about 1.5 to about 80, "c" has a value of 0 to about 1.0, "d" has a value of about 8 to about 40, "e" has a value of about 25 to about 4000.

Yet another embodiment of the invention is a hydrocarbon conversion process using the above-described zeolite. The process comprises contacting the hydrocarbon with the zeolite at conversion conditions to give a converted hydrocarbon.

DETAILED DESCRIPTION OF THE INVENTION

Applicants have prepared an aluminosilicate zeolite whose topological structure is similar to MWW as described in *Atlas of Zeolite Framework Types*, which is maintained by the International Zeolite Association Structure Commission at http://topaz.ethz.ch/IZA-SC/StdAtlas.htm, which has been designated UZM-37. As will be shown in detail, UZM-37 is different from MWW in a number of its characteristics. The instant microporous crystalline zeolite (UZM-37) has an empirical composition in the as-synthesized form and on an anhydrous basis expressed by the empirical formula:

$$M_m{}^+R_r{}^+Al_{1-x}E_xSi_yO_z$$

where M represents sodium or a combination of sodium/potassium or lithium/strontium exchangeable cations. R is a singly charged organoammonium cation, examples of which include but are not limited to the propyltrimethylammonium cation, iso-propyltrimethyl cation, dimethyldipropylammonium cation (DMDPA$^+$), choline [(CH$_3$)$_3$N(CH$_2$)$_2$OH]$^+$, ETMA$^+$, DEDMA$^+$, trimethylbutylammonium, dimethyldiethanolammonium, methyltripropylammonium, TEA$^+$, TPA$^+$ and mixtures thereof and "r" is the mole ratio of R to (Al+E) and varies from about 0.25 to about 2.0 while "m" is the mole ratio of M to (Al+E) and varies from about 0.05 to about 3. The ratio of silicon to (Al+E) is represented by "y" which varies from about 8 to about 40. E is an element which is tetrahedrally coordinated, is present in the framework and is selected from the group consisting of gallium, iron and boron. The mole fraction of E is represented by "x" and has a value from 0 to about 1.0, while "z" is the mole ratio of O to (Al+E) and is given by the equation:

$$z=(m \cdot n + r + 3 + 4 \cdot y)/2.$$

Where M is only one metal, then the weighted average valence is the valence of that one metal, i.e. +1 or +2. However, when more than one M metal is present, the total amount of:

$$M_m{}^{n+}M_{m1}{}^{(n1)+}+M_{m2}{}^{(n2)+}+M_{m3}{}^{(n3)+}+\ldots$$

and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

The microporous crystalline zeolite, UZM-37, is prepared by a hydrothermal crystallization of a reaction mixture prepared by combining reactive sources of M, R, aluminum, silicon and optionally E. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica and alkali silicates. Sources of the E elements include but are not limited to alkali borates, boric acid, precipitated gallium oxyhydroxide, gallium sulfate, ferric sulfate, and ferric chloride. Sources of the M metals, potassium and sodium, include the halide salts, nitrate salts, acetate salts, and hydroxides of the respective alkali metals. R is an organoammonium cation selected from the group consisting of propyltrimethylammonium, isopropyltrimethylammonium, dimethyldipropylammonium, choline, ETMA, DEDMA, TEA, TPA, trimethylbutylammonium, dimethyldiethanolammonium and mixtures thereof, and the sources include the hydroxide, chloride, bromide, iodide and fluoride compounds. Specific examples include without limitation propyltrimethylammonium hydroxide, propyltrimethylammonium chloride, propyltrimethylammonium bromide, iso-propyltrimethylammonium hydroxide, iso-propyltrimethylammonium chloride, iso-propyltrimethylammonium bromide, dimethyldipropylammonium hydroxide, ethyltrimethylammonium hydroxide, diethyldimethylammonium hydroxide, tetraethylammonium hydroxide, tetrapropylammonium hydroxide.

The reaction mixture containing reactive sources of the desired components can be described in terms of molar ratios of the oxides by the formula:

$$aM_2O:bR_{2/p}O:1\text{-}cAl_2O_3:cE_2O_3:dSiO_2:eH_2O$$

where "a" varies from about 0.05 to about 1.25, "b" varies from about 1.5 to about 80, "c" varies from 0 to 1.0, "d" varies from about 8 to about 40, and "e" varies from about 25 to about 4000. If alkoxides are used, it is preferred to include a distillation or evaporative step to remove the alcohol hydrolysis products. The reaction mixture is now reacted at a temperature of about 150° C. to about 200° C., about 165° C. to about 185° C., or about 170° C. to about 180° C., for a period of about 1 day to about 3 weeks and preferably for a time of about 5 days to about 12 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. It should be pointed out that UZM-37 seeds can optionally be added to the reaction mixture in order to accelerate the formation of the zeolite.

A preferred synthetic approach to make UZM-37 utilizes the charge density mismatch concept, which is disclosed in U.S. Pat. No. 7,578,993 and *Studies in Surface Science and Catalysis*, (2004), Vol. 154A, 364-372. The method disclosed in U.S. Pat. No. 7,578,993 employs quaternary ammonium hydroxides to solubilize aluminosilicate species, while crystallization inducing agents such as alkali and alkaline earth metals and more highly charged organoammonium cations are often introduced in a separate step. Once some UZM-37 seeds have been generated using this approach, the seeds can be used in a single step synthesis of UZM-37, using, for example, a combination of propyltrimethylammonium hydroxide and the alkali cations. The use of commercially available propyltrimethylammonium hydroxide to prepare UZM-37 offers a great economic advantage over previously employed structure directing agents such as hexamethylimine used to prepare aluminosilicates with the MWW topology. Additionally, propyltrimethyl ammonium hydroxide can be employed as the hydroxide or the chloride in concert with other inexpensive organoammonium hydroxides using the charge density mismatch concept to reduce costs even further.

The UZM-37 aluminosilicate zeolite, which is obtained from the above-described process, is characterized by the x-ray diffraction pattern, having at least the d-spacings and relative intensities set forth in Table A below.

TABLE A

| 2θ | d (Å) | I/Io % |
|---|---|---|
| 3.22-3.48 | 25.35-27.44 | m |
| 6.62-6.92 | 12.76-13.34 | m |
| 7.12-7.39 | 11.93-12.4 | s-vs |
| 7.92-8.32 | 10.61-11.15 | m |
| 8.64-8.81 | 10.01-10.22 | m |
| 9.71-9.85 | 8.97-9.09 | m |
| 12.75-12.78 | 6.92-6.93 | w |
| 13.39-13.72 | 6.44-6.6 | w |
| 14.34-14.5 | 6.1-6.17 | w |
| 20.13-20.2 | 4.39-4.4 | m |
| 21.56-21.64 | 4.1-4.11 | m |
| 22.14-22.28 | 3.98-4.01 | m |
| 23.09-23.35 | 3.8-3.84 | m |
| 23.95-23.97 | 3.7-3.71 | w-m |
| 24.92-25.19 | 3.53-3.57 | m |
| 25.92-26.21 | 3.39-3.43 | vs |
| 26.7-26.77 | 3.32-26.7 | m |
| 28.99-29.32 | 3.04-3.07 | w-m |
| 31.51-31.64 | 2.82-2.83 | w |
| 33.3-33.69 | 2.65-2.68 | w |
| 37.68-37.94 | 2.36-2.38 | w |
| 46.05-46.29 | 1.95-1.96 | w |
| 48.78-48.94 | 1.85-1.86 | w |

As will be shown in detail in the examples, the UZM-37 material is thermally stable up to a temperature of at least 600° C. and in another embodiment, up to about 700° C. The characteristic diffraction lines associated with typical calcined UZM-37 samples are shown in Table B.

TABLE B

| 2θ | d (Å) | I/Io % |
|---|---|---|
| 7.28-7.45 | 11.84-12.1 | s-vs |
| 8.04-8.18 | 10.79-10.98 | m |
| 10.02-10.21 | 8.64-8.82 | m |
| 12.91-13.15 | 6.72-6.81 | m |
| 14.52-14.69 | 6.02-6.08 | m-s |
| 19-19.16 | 4.62-4.66 | w |
| 19.79-19.92 | 4.45-4.48 | w-m |
| 20.36-20.53 | 4.32-4.33 | m |
| 22.03-22.15 | 4-4.03 | m |
| 22.8-22.9 | 3.88-3.89 | s-vs |
| 23.82-24.02 | 3.7-3.73 | m |
| 25.24-25.3 | 3.51-3.52 | m |
| 26.2-26.36 | 3.37-3.39 | vs |
| 27.06-27.24 | 3.27-3.29 | m |
| 27.88-27.97 | 3.18-3.19 | m |
| 28.15-28.33 | 3.14-3.16 | m |

As synthesized, the UZM-37 material will contain some of the exchangeable or charge balancing cations in its pores. These exchangeable cations can be exchanged for other cations, or in the case of organic cations, they can be removed by heating under controlled conditions. The UZM-37 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Properties that are modified include porosity, adsorption, Si/Al ratio, acidity, thermal stability, etc.

The UZM-37 compositions which are modified by one or more techniques described in the '975 patent (herein UZM-37HS) are described by the empirical formula on an anhydrous basis of:

$$M1_a^{n+}Al_{(1-x)}E_xSi_{y'}O_{z''}$$

where M1 is at least one exchangeable cation selected from the group consisting of alkali, alkaline earth metals, rare earth metals, ammonium ion, hydrogen ion and mixtures thereof, "a" is the mole ratio of M1 to (Al+E) and varies from about 0.05 to about 50, "n" is the weighted average valence of M1 and has a value of about +1 to about +3, E is an element selected from the group consisting of gallium, iron, boron, and mixtures thereof, "x" is the mole fraction of E and varies from 0 to 1.0, y' is the mole ratio of Si to (Al+E) and varies from greater than about 4 to virtually pure silica and z' is the mole ratio of O to (Al+E) and has a value determined by the equation:

$$z'=(a\cdot n+3+4\cdot y')/2$$

By virtually pure silica is meant that virtually all the aluminum and/or the E metals have been removed from the framework. It is well know that it is virtually impossible to remove all the aluminum and/or E metal. Numerically, a zeolite is virtually pure silica when y' has a value of at least 3,000, preferably 10,000 and most preferably 20,000. Thus, ranges for y' are from 4 to 3,000 preferably greater than 10 to about 3,000; 4 to 10,000 preferably greater than 10 to about 10,000 and 4 to 20,000 preferably greater than 10 to about 20,000.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The crystalline UZM-37 zeolite of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

The UZM-37 zeolite of this invention can also be used as a catalyst or catalyst support in various hydrocarbon conversion processes. Hydrocarbon conversion processes are well known in the art and include cracking, hydrocracking, alkylation of both aromatics and isoparaffin, isomerization of paraffin and poly-alkylbenzenes such as xylene, trans-alkylation of poly-alkybenzene with benzene or mono-alkybenzenes, disproportionation of mono-alkybenzenes, polymerization, reforming, hydrogenation, dehydrogenation, dealkylation, hydration, dehydration, isomerization of aromatics, alkylation of olefins with isoparaffin, olefin dimerization, olefin oligomerization, catalytic cracking, and dewaxing. Specific reaction conditions and the types of feeds which can be used in these processes are set forth in U.S. Pat. No. 4,310,440 and U.S. Pat. No. 4,440,871, which are hereby incorporated by reference.

One hydrocarbon conversion process that may be carried out using UZM-37 as a catalyst or catalyst support is catalytic cracking process using feedstocks such as gas oils, heavy naphthas, deasphalted crude oil residua, etc. with gasoline being the principal desired product. Temperature conditions of about 454° C. to about 593° C. (about 850° F. to about 1100° F.), LHSV values of 0.5 to 10 and pressure conditions of from about 0 to about 344 kPa g (about 0 to 50 psig) are suitable.

Another hydrocarbon conversion process that may be carried out using UZM-37 as a catalyst or catalyst support is the alkylation of aromatics which usually involves reacting an aromatic ($C_2$ to $C_{12}$), especially benzene, with a monoolefin to produce a alkyl substituted aromatic. The process is carried out at an aromatic:olefin (e.g., benzene:olefin) ratio of between 1:1 and 30:1, a olefin LHSV of about 0.3 to about 10 hr$^{-1}$, a temperature of about 80° to about 300° C. and pressures of about 1379 kPa g to about 6895 kPa g (about 200 to about 1000 psig). Further details on apparatus may be found in U.S. Pat. No. 4,870,222 which is incorporated by reference.

Still another hydrocarbon conversion process that may be carried out using UZM-37 as a catalyst or catalyst support is the alkylation of isoparaffins with olefins to produce alkylates suitable as motor fuel components is carried out at temperatures of −30° to 100° C., pressures from about atmospheric to about 6,895 kPa (1,000 psig) and a weight hourly space velocity (WHSV) of 0.1 to about 120. Details on paraffin alkylation may be found in U.S. Pat. No. 5,157,196 and U.S. Pat. No. 5,157,197, which are incorporated by reference.

The structure of the UZM-37 zeolite of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$," being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of 100×I/$I_o$, the above designations are defined as:

$w=0-15; m=15-60; s=60-80$ and $vs=80-100$

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In the following examples, the BET surface area and micropore volumes of the materials were determined using UOP Method 964-98.

In order to more fully illustrate the invention, the following examples are set forth. It is to be understood that the examples are only by way of illustration and are not intended as an undue limitation on the broad scope of the invention as set forth in the appended claims.

Example 1

An aluminosilicate solution was prepared by first mixing 39.81 aluminum hydroxide (28.22% Al) and 1371.36 g propyltrimethylammonium hydroxide, 21.9% solution, with vigorous stirring. After thorough mixing, 952.5 g of Ludox™ AS-40 (39.8% $SiO_2$) was added. The reaction mixture was homogenized for an additional hour with a high speed mechanical stirrer and placed in an oven at 100° C. overnight. Analysis showed the resulting aluminosilicate solution contained 7.58 wt. % Si and 0.49 wt. % Al yielding a Si/Al ratio of 14.86.

To a 1000 g portion of the aluminosilicate solution prepared in Example 1, an aqueous NaCl solution containing 21.16 g of NaCl (98%) dissolved in 100.0 g distilled water was added with vigorous stirring and the reaction mixture was homogenized for an additional 30 minutes. A 1067 g portion of the reaction mixture was transferred to a 2000 ml Parr stainless steel autoclave which was heated to 175° C. and maintained at that temperature for 168 hrs. The solid product was recovered by filtration, washed with de-ionized water, and dried at 100° C.

The product was identified as UZM-37 by xrd. Representative diffraction lines observed for the product are shown in Table 1. The product composition was determined by elemental analysis to consist of the following mole ratios: Si/Al=13.02, Na/Al=0.57, N/Al=1.32, C/N=5.94. A portion of the material was calcined by ramping to 600° C. in air for 2 hrs followed by a 2 hr dwell in air. The BET surface area was found to be 378 m2/g and the micropore volume was 0.16 cc/g.

TABLE 1

| 2θ | d(Å) | I/$I_o$ % |
|---|---|---|
| 3.37 | 26.12 | m |
| 6.77 | 13.03 | m |
| 7.26 | 12.16 | s |
| 8.16 | 10.82 | m |
| 8.64 | 10.22 | m |
| 9.71 | 9.09 | m |
| 12.75 | 6.93 | w |
| 14.44 | 6.12 | w |
| 20.15 | 4.4 | m |
| 21.64 | 4.1 | m |
| 22.14 | 4.01 | m |
| 23.3 | 3.81 | m |
| 23.95 | 3.71 | m |
| 25.08 | 3.54 | m |
| 26.07 | 3.41 | vs |
| 26.72 | 3.33 | m |
| 29.26 | 3.04 | w |
| 31.62 | 2.82 | w |
| 33.69 | 2.65 | w |
| 37.88 | 2.37 | w |
| 46.15 | 1.96 | w |
| 48.83 | 1.86 | w |
| 51.3 | 1.77 | w |

Scanning Electron Microscopy (SEM) revealed crystals of plate shaped morphology, approximately 400 nm by 600 nm in size. This sample was calcined at 600° C. for 2 hrs under air. Representative diffraction lines observed for the product are shown in Table 2.

TABLE 2

| 2θ | d(Å) | I/$I_o$ % |
|---|---|---|
| 4.06 | 21.74 | w |
| 7.28 | 12.13 | s |
| 8.12 | 10.87 | m |
| 10.04 | 8.8 | m |
| 12.91 | 6.84 | m |
| 14.52 | 6.09 | m |
| 16.03 | 5.52 | m |
| 19.16 | 4.62 | w |

TABLE 2-continued

| 2θ | d(Å) | I/I₀ % |
|---|---|---|
| 20.36 | 4.35 | m |
| 22.06 | 4.02 | m |
| 22.8 | 3.89 | s |
| 24.02 | 3.7 | m |
| 25.3 | 3.51 | m |
| 26.2 | 3.39 | vs |
| 27.09 | 3.28 | m |
| 27.97 | 3.18 | w |
| 46.54 | 1.94 | w |

Example 2

To a 1000 g portion of the aluminosilicate solution prepared in Example 1, an aqueous NaCl solution containing 15.87 g of NaCl (98%) dissolved in 100.0 g distilled water was added with vigorous stirring and the reaction mixture was homogenized for an additional 30 minutes. A 1050 g portion of the reaction mixture was transferred to a 2000 ml Parr stainless steel autoclave which was heated to 175° C. and maintained at that temperature for 168 hrs. The solid product was recovered by filtration, washed with de-ionized water, and dried at 100° C.

The product was identified as UZM-37 by xrd. Representative diffraction lines observed for the product are shown in Table 3. The product composition was determined by elemental analysis to consist of the following mole ratios: Si/Al=13.21, Na/Al=0.45, N/Al=1.37, C/N=5.90. A portion of the material was calcined by ramping to 600° C. in air for 2 hrs followed by a 2 hr dwell in air. The BET surface area was found to be 401 m²/g and the micropore volume was 0.164 cc/g. Scanning Electron Microscopy (SEM) revealed crystals of plate shaped morphology, approximately 500 nm by 600 nm in size.

TABLE 3

| 2θ | d(Å) | I/I₀ % |
|---|---|---|
| 3.31 | 26.59 | m |
| 6.77 | 13.02 | m |
| 7.24 | 12.19 | vs |
| 8.12 | 10.87 | m |
| 8.81 | 10.01 | m |
| 9.28 | 9.52 | m |
| 12.78 | 6.92 | w |
| 13.58 | 6.51 | w |
| 15.84 | 5.58 | w |
| 20.19 | 4.39 | m |
| 21.63 | 4.1 | m |
| 22.18 | 4 | m |
| 22.76 | 3.9 | m |
| 23.35 | 3.8 | m |
| 23.53 | 3.77 | m |
| 23.77 | 3.73 | m |
| 23.97 | 3.7 | w |
| 25.11 | 3.54 | m |
| 26.07 | 3.41 | vs |
| 26.76 | 3.32 | m |
| 28.99 | 3.07 | w |
| 31.64 | 2.82 | w |
| 33.69 | 2.65 | w |
| 37.82 | 2.37 | w |
| 46.29 | 1.95 | w |
| 48.94 | 1.85 | w |
| 51.62 | 1.76 | w |

Example 3

An aluminosilicate solution was prepared by first mixing 13.27 g aluminum hydroxide (28.22% Al) and 457.12 g propyltrimethylammonium hydroxide, 21.9% solution, with vigorous stirring. After thorough mixing, 317.50 g of Ludox™ AS-40 (39.8% SiO₂) was added. The reaction mixture was homogenized for an additional hour with a high speed mechanical stirrer and placed in an oven at 100° C. overnight. Analysis showed the resulting aluminosilicate solution contained 7.71 wt. % Si and 0.49 wt. % Al yielding a Si/Al ratio of 15.15.

A 790 g portion of the aluminosilicate solution was placed in a container and an aqueous NaCl solution containing 16.71 g of NaCl (98%) dissolved in 80.0 g distilled water was added with vigorous stirring and the reaction mixture was homogenized for an additional 30 minutes. A 850 g portion of the reaction mixture was transferred to a 2000 ml Parr stainless steel autoclave which was heated to 175° C. and maintained at that temperature for 144 hrs. The solid product was recovered by filtration, washed with de-ionized water, and dried at 100° C.

The product was identified as UZM-37 by xrd. Representative diffraction lines observed for the product are shown in Table 4. The product composition was determined by elemental analysis to consist of the following mole ratios: Si/Al=12.86, Na/Al=0.55, N/Al=1.40, C/N=5.7. A portion of the material was calcined by ramping to 600° C. in air for 2 hrs followed by a 2 hr dwell in air. The BET surface area was found to be 342 m²/g and the micropore volume was 0.14 cc/g.

TABLE 4

| 2θ | d(Å) | I/I₀ % |
|---|---|---|
| 3.22 | 27.44 | m |
| 6.62 | 13.34 | m |
| 7.12 | 12.40 | s |
| 7.92 | 11.15 | m |
| 8.79 | 10.04 | m |
| 9.85 | 8.97 | m |
| 13.39 | 6.60 | w |
| 14.34 | 6.17 | w |
| 20.13 | 4.40 | m |
| 21.56 | 4.11 | m |
| 22.18 | 4.00 | m |
| 23.25 | 3.82 | m |
| 24.92 | 3.57 | m |
| 25.92 | 3.43 | vs |
| 26.7 | 3.33 | m |
| 29.01 | 3.07 | m |
| 31.51 | 2.83 | w |
| 33.65 | 2.68 | w |
| 37.68 | 2.38 | w |
| 46.05 | 1.96 | w |
| 48.78 | 1.86 | w |

Example 4

An aluminosilicate solution was prepared by first mixing 13.27 g aluminum hydroxide (28.22% Al) and 457.12 g propyltrimethylammonium hydroxide, 21.9% solution, with vigorous stirring. After thorough mixing, 317.50 g of Ludox™ AS-40 (39.8% SiO₂) was added. The reaction mixture was homogenized for an additional hour with a high speed mechanical stirrer and placed in an oven at 100° C. overnight. Analysis showed the resulting aluminosilicate solution contained 7.47 wt. % Si and 0.47 wt. % Al yielding a Si/Al ratio of 15.3.

A 55 g portion of the aluminosilicate solution was placed in a container and an aqueous NaOH and KOH solution containing 0.19 g of NaOH (98%) and 0.26 g KOH dissolved in 10.0 g distilled water was added with vigorous stirring and the reaction mixture was homogenized for an additional 30 minutes. A 20 g portion of the above reaction mixture was transferred to a 45 ml Parr stainless steel autoclave which was heated to 175° C. and maintained at that temperature for 240 hrs. The solid product was recovered by filtration, washed with de-ionized water, and dried at 100° C.

The product was identified as UZM-37 by xrd. Representative diffraction lines observed for the product are shown in Table 5. The product composition was determined by elemental analysis to consist of the following mole ratios: Si/Al=12.68, Na/Al=0.10, K/Al=0.07, N/Al=1.13, C/N=6.0. A portion of the material was calcined by ramping to 600° C. in air for 2 hrs followed by a 2 hr dwell in air. The BET surface area was found to be 352 m²/g and the micropore volume was 0.14 cc/g.

TABLE 5

| 2θ | d(Å) | I/I₀ % |
|---|---|---|
| 3.48 | 25.35 | m |
| 6.92 | 12.76 | m |
| 7.39 | 11.93 | s |
| 8.32 | 10.61 | m |
| 9.83 | 8.98 | m |
| 13.72 | 6.44 | w |
| 14.50 | 6.10 | w |
| 20.20 | 4.39 | m |
| 22.28 | 3.98 | m |
| 23.09 | 3.84 | m |
| 23.95 | 3.71 | m |
| 25.19 | 3.53 | m |
| 26.21 | 3.39 | vs |
| 26.77 | 3.32 | m |
| 29.32 | 3.04 | w |
| 33.3 | 2.68 | w |
| 37.94 | 2.36 | w |

The invention claimed is:

1. A hydrocarbon conversion process comprising contacting a hydrocarbon stream with a catalyst at hydrocarbon conversion conditions to give a converted product, the catalyst comprising a modified UZM-37 microporous crystalline zeolite, wherein the modified UZM-37 has a three-dimensional framework of at least AlO₂ and SiO₂ tetrahedral units and an empirical composition on an anhydrous basis expressed by an empirical formula of:

$$M1_a^{n+}Al_{(1-x)}E_xSi_{y'}O_{z'}$$

where M1 is at least one exchangeable cation selected from the group consisting of alkali, alkaline earth metals, rare earth metals, ammonium ion, hydrogen ion and mixtures thereof, "a" is the mole ratio of M1 to (Al+E) and varies from about 0.05 to about 50, "n" is the weighted average valence of M1 and has a value of about +1 to about +3, E is an element selected from the group consisting of gallium, iron, boron, and mixtures thereof, "x" is the mole fraction of E and varies from 0 to 1.0, y' is the mole ratio of Si to (Al+E) and varies from greater than about 4 to virtually pure silica and z' is the mole ratio of O to (Al+E) and has a value determined by the equation:

$$z'=(a \cdot n+3+4 \cdot y')/2$$

and is characterized in that it has the x-ray diffraction pattern having at least the d-spacings and intensities set forth in Table A

TABLE A

| 2θ | d (Å) | I/Io % |
|---|---|---|
| 3.22-3.48 | 25.35-27.44 | m |
| 6.62-6.92 | 12.76-13.34 | m |
| 7.12-7.39 | 11.93-12.4 | s-vs |
| 7.92-8.32 | 10.61-11.15 | m |
| 8.64-8.81 | 10.01-10.22 | m |
| 9.71-9.85 | 8.97-9.09 | m |
| 12.75-12.78 | 6.92-6.93 | w |
| 13.39-13.72 | 6.44-6.6 | w |
| 14.34-14.5 | 6.1-6.17 | w |
| 20.13-20.2 | 4.39-4.4 | m |
| 21.56-21.64 | 4.1-4.11 | m |
| 22.14-22.28 | 3.98-4.01 | m |
| 23.09-23.35 | 3.8-3.84 | m |
| 23.95-23.97 | 3.7-3.71 | w-m |
| 24.92-25.19 | 3.53-3.57 | m |
| 25.92-26.21 | 3.39-3.43 | vs |
| 26.7-26.77 | 3.32-26.7 | m |
| 28.99-29.32 | 3.04-3.07 | w-m |
| 31.51-31.64 | 2.82-2.83 | w |
| 33.3-33.69 | 2.65-2.68 | w |
| 37.68-37.94 | 2.36-2.38 | w |
| 46.05-46.29 | 1.95-1.96 | w |
| 48.78-48.94 | 1.85-1.86 | w | and is thermally stable up to a temperature of at least 600° C. and has a BET surface area of less than about 420 m²/g, wherein the hydrocarbon conversion process is selected from the group consisting of alkylation, de-alkylation, trans-alkylation of aromatics, isomerization of aromatics, alkylation of olefins with isoparaffin, olefin dimerization, olefin oligomerization, catalytic cracking, and dewaxing.

* * * * *